US007446243B2

(12) United States Patent  (10) Patent No.: US 7,446,243 B2
Gupta et al.  (45) Date of Patent: Nov. 4, 2008

(54) HIGH HERB, PHYLLANTHIN AND HYPOPHYLLANTHIN YIELDING CULTIVAR OF *PHYLLANTHUS AMARUS* 'CIM-JEEVAN'

(75) Inventors: Anil Kumar Gupta, Uttar Pradesh (IN); Suman Preet Singh Khanuja, Uttar Pradesh (IN); Madan Mohan Gupta, Uttar Pradesh (IN); Ajit Kumar Shasany, Uttar Pradesh (IN); Neeraj Jain, Uttar Pradesh (IN); Ram Kishor Verma, Uttar Pradesh (IN); Mahendra Pandurang Darokar, Uttar Pradesh (IN); Guru Das Bagchi, Uttar Pradesh (IN); Sushil Kumar, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 745 days.

(21) Appl. No.: 10/647,114

(22) Filed: Aug. 25, 2003

(65) Prior Publication Data

US 2005/0050593 A1  Mar. 3, 2005

(51) Int. Cl.
*A01H 5/00* (2006.01)
(52) U.S. Cl. .................................................. 800/298
(58) Field of Classification Search ................. 800/298
See application file for complete search history.

*Primary Examiner*—Kent L Bell
(74) *Attorney, Agent, or Firm*—Foley & Lardner LLP

(57) ABSTRACT

The present invention relates to a cultivar of *Phyllanthus amarus* 'CIM-Jeevan', producing high amount of herb, phyllanthin and hypophyllanthin, wherein said cultivar is developed through γ-irradiation of superior germplasm, the said plant produces high amount of herbage yield ranging between 1.0-1.15 kg per sqm fresh total plant herb, possesses high vegetative erect growth with a height ranging between 60 to 65 cm, produces phyllanthin ranging between 0.70-0.77% in dry herb, produces hypophyllanthin ranging between 0.32-0.37% in dry herb, and shows seed germination of about 90%.

1 Claim, 1 Drawing Sheet

A plant of 'CIM-Jeevan' in the field

Figure 1: A plant of 'CIM-Jeevan' in the field
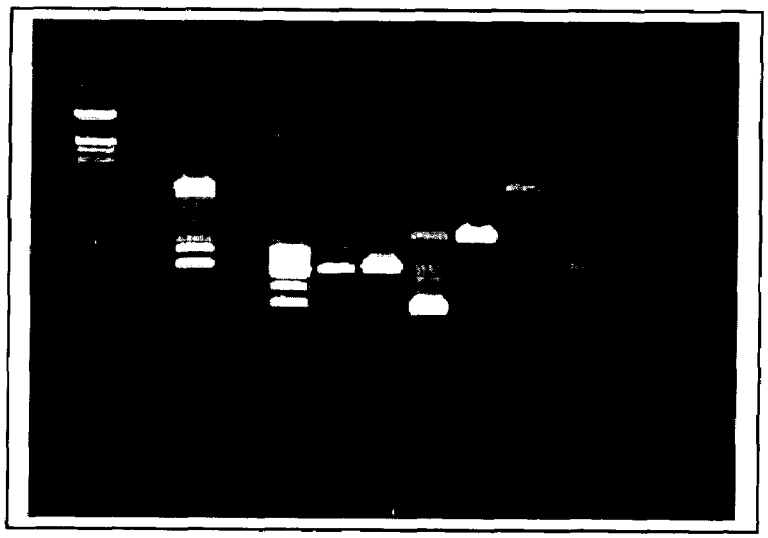
Figure 2: Unique RAPD profile of the cultivar 'CIM-Jeevan'

US 7,446,243 B2

HIGH HERB, PHYLLANTHIN AND HYPOPHYLLANTHIN YIELDING CULTIVAR OF *PHYLLANTHUS AMARUS* 'CIM-JEEVAN'

FIELD OF THE PRESENT INVENTION

The present invention relates to a cultivar of *Phyllanthus amarus* 'CIM-Jeevan', producing high amount of herb, phyllanthin and hypophyllanthin, wherein said cultivar is developed through γ-irradiation of superior germplasm, the said plant produces high amount of herbage yield ranging between 1.0-1.15 kg per sqm fresh total plant herb, possesses high vegetative erect growth with a height ranging between 60 to 65 cm, produces phyllanthin ranging between 0.70-0.77% in dry herb, produces hypophyllanthin ranging between 0.32-0.37% in dry herb, and shows seed germination of about 90%.

Seeds of the plant *Phyllanthus amarus* that produce plants designated "CIM-Jeevan" have been deposited in the "National Gene Bank," funded by Government of India at CIMAP, with gene bank accession number "CIMAP 1421." They are readily traceable, retraceable and available to the public on Demands. There will be no restriction to the availability of the seeds to the public. The viability of the seeds is checked every year and redeposited in the gene bank, which will continue indefinitely.

BACKGROUND AND PRIOR ART OF PRESENT INVENTION

The genus *Phyllanthus* L. of the family Euphorbiaceae consists of about 800 species, of which 200 are American, 100 African, 70 Madagascar and the remaining Asian and Australasian. *P. amarus* is a highly important medicinal plant species due to its antiviral properties useful against hepatitis infection. The species is also used in stomach troubles like dyspepsia, colic, diarrhoea, dysentery; dropsy and urinogenital problems and also as external application for oedematous swelling and inflammation. It is also used as an ingredient in many Ayurvedic preparations especially those used in the treatment of jaundice. This species is distributed to all over India and is considered as most widely occuring species of *Phyllanthus* in India. The plant is being collected from wild to be used in medicinal preparation in which the chemical components vary leading to variation in the quality. So the need was felt to develop a high yielding cultivar for wide spread cultivation in one hand and to save the wild germplasm on the other. For this reason-planned breeding programme was undertaken to develop a cultivar of *Phyllanthus amarus* with high yield and defined marker chemical like phyllanthin and hypophyllanthin.

DETAILED DESCRIPTION OF THE PRESENT INVENTION

The present invention relates to a cultivar of *Phyllanthus amarus* 'CIM-Jeevan', producing high amount of herb, phyllanthin and hypophyllanthin, wherein said cultivar is developed through γ-irradiation of superior germplasm, the said plant produces high amount of herbage yield ranging between 1.0-1.15 kg per sqm fresh total plant herb, possesses high vegetative erect growth with a height ranging between 60 to 65 cm, produces phyllanthin ranging between 0.70-0.77% in dry herb, produces hypophyllanthin ranging between 0.32-0.37% in dry herb, and shows seed germination of about 90%.

The main embodiment of the present invention relates to a cultivar of *Phyllanthus amarus* 'CIM-Jeevan', producing high amount of herb, phyllanthin and hypophyllanthin, wherein said cultivar is developed through γ-irradiation of superior germplasm, having following characters:

a. the said plant produces high amount of herbage yield ranging between 1.0-1.15 kg per sqm fresh total plant herb,
b. the said plant possesses high vegetative erect growth with a height ranging between 60 to 65 cm,
c. the said plant has distinct molecular profile established by Random Amplified Polymorphic DNA (RAPD),
d. the said plant has leaves with following characteristics,
   Color: greenish leaves with upper surface (127A) and lower surface (136D),
   Surface: Smooth,
   Shape: elliptic oblong to obvate,
   Margin: ciliate,
   Tip: obtuse,
   Base: Obtuse,
   Petiole length: 0.3-0.7 mm,
   Length: 6 to 10 mm, and
   Width: 4 to 5 mm
e. the said plant has stem with following characteristics,
   Terete,
   Smooth,
   Green (138C)
   Young parts are rough
f. the said plant has flowers with perianth having the following characters:
   Lobes 5, sub-equal, elliptic or oblong, Disc 5 roundish
   Stamens: 3, free, filaments connate in a column, anther sessile
   Style: 3, spreading, stigma bi-fid, divergent
g. the said plant has fruit with the following characters:
   Capsule,
   Obvate-rounded,
   Yellow green group (144 D)
h. the said plant has seeds with the following characters:
   Triangular,
   longitudinal ribs,
   transverse striate on back,
   weight of 1000-seed: about 1.8 g.
i. the said plant produce phyllanthin ranging between 0.70-0.77% in dry herb,
j. the said plant produce hypophyllanthin ranging between 0.32-0.37% in dry herb,
k. the said plant produce average dry seed per plant of about 4.1 in grams,
l. the said plant produce average dry leaves per plant of about 5.75 in grams,
m. the said plant produce average dry biomass per plant of about 11 in grams,
n. the said plant produce average fresh biomass per plant at harvest of about 55 in grams,
o. the said plant shows seed germination of about 90%,
p. the said plant is an annual herb.

BRIEF DESCRIPTION OF THE ACCOMPANYING DRAWINGS

FIG. 1 shows a plant of CIM-Jeevan in the field (30 days old).

FIG. 2 shows the unique RAPD profile of the cultivar. Lane 1: 1 Hind III marker, Lane 2 to 11 profiles with AAATCGGAGC, TGCGCGATCG, AACGTACGCG, CGGGATCCGC, GCGAATTCCG, CCCTGCAGGC, CCAAGCTTGC, AAGATAGCGG, GGATCTGAAC, GGACTCCACG primers.

*Phyllanthus amarus* (Family: Euphorbiaceae) occurs widely with distribution all over India. It is a highly important medicinal plant species due to its hepatoprotective and antiviral properties useful against liver infection. It is also used in stomach troubles like dyspepsia, colic, diarrhoea, dysentery; dropsy and urinogenital problems and also as external application for oedematous swelling, inflammation and as an ingredient in many Ayurvedic preparations especially those used in the treatment of jaundice. Traditionally, the plant is collected from wild to be used in formulations in which the chemical components vary leading to variation in the quality. The need was therefore felt to develop a high yielding cultivar for large-scale cultivation saving the wild germplasm. The cultivar CIM-Jeevan of *Phyllanthus amarus* has been developed by CIMAP through directed breeding efforts (using gama radiation) having high herb yield (1-1.15 kg per sqm) and defined marker chemicals profile like phyllanthin (0.70-0.77%) and hypophyllanthin (0.32-0.37%) for quality validation.

The invention is related to a cultivar of *Phyllanthus amarus* having the designation 'CIM-Jeevan', produced by recurrent selection of γ-rays irradiated mutants of a high herb yielding parent selected from the germplasm. The invention is also related to the reasultant selection from the mutant maintaining the character of high herb, phyllanthin and hypophyllanthin yield. This invention thus relates to the seeds, plants and plant parts of CIM-Jeevan and its components, to plants regenerated from tissue culture of the plants of CIM-Jeevan, to a method of producing CIM-Jeevan, and to a method for producing high herb, phyllanthin, hypophyllanthin yielding plant using 'CIM-Jeevan' as a parent.

Breeding history—In the year 1999 extensive collection of *Phyllanthus amarus* was made and were grown in the field. By visual observation of high growth rate one collection was chosen. In the search of an improved cultivar, which is superior to other genotypes of *Phyllanthus amarus*, attempt was made to induce the mutation through radiation the sublethal ☐ gamma rays in early 2000. Out of different doses of dose 10KR was choosen for itrradiation. Since 3 crops of bhumi-amliki (*Phyllanthus amarus*) are possible in a year, it provided ample opportunity for fast track breeding. In the same year the irradiation-exposed seeds were sown and seedlings were transplanted in the field with an objective of selecting some genetically reshuffled apparently improved lines for herb yield. Four phenotypic mutants were selected in M1. The M1 selected mutants were grown to raise the M2, which were analyzed for phyllanthin and hypophyllanthin content. The seeds of the plant producing highest amount of phyllanthin and hypophyllanthin were bulked and grown in the next generation. The seed bulking and screening based on morphological similarity and high herb yield, phyllanthin and hypophyllanthin content was continued for the next generation.

During screening and experimentation individual strains were maintained in seed plots with an isolation distance of 100 m² and seeds obtained from these seed plots were used in growing the plants for evaluation. During the evaluation trials 10 plants from each strains were evaluated through profiling the population DNA and comparing among each other for maintenance of purity and stability through generations. The plants when grown in isolation as mentioned are self-pollinated and maintain the stability and purity as observed from the morphological, phyllanthin and hypophyllanthin content and DNA profiles.

Evaluation trials: The Initial Evaluation Trial (IET) evaluations were carried out in randomised block design (RBD) with three replications in 0.90 m² plots for each treatment during year 2001. The Initial Evaluation Trial (IET) was repeated in the same year and after confirming the stable behaviour of these mutants; they were evaluated in Advanced Varietal Trial (AVT) with a larger plot size. The AVT was repeated in 2002 again. The AVT evaluations were carried out in randomised block design (RBD) with three replications in 1.80 m² plots for each treatment during year 2002. A common check (a genotype grown extensively for medicinal use in Ayurvedic formulations) 'CIM/PAG-1' was taken for comparison in all the evaluation trials. The stabilized mutant line 'CIMAP/PA 36' (now onward referred as 'CIM-Jeevan') produced higher biomass yield than the check variety. The characteristics and yield evaluation data are presented in table 1 and table 2 respectively.

TABLE 1

Growth and yield parameters of variety
(Based on data on ten representative plants)

| Characters | CIM-Jeevan | Check |
| --- | --- | --- |
| Plant height (at 60 days after Transplanting) in cm | 60-65 | 50-55 |
| Fresh biomass/plant at harvest in grams | 55 | 39 |
| Dry biomass/plant in g | 11 | 07 |
| Dry leaves/plant in g | 5.75 | 3.2 |
| Dry seed/plant in g | 4.1 | 2.9 |
| !000-seed weight in g | 1.8 | 1.8 |
| Seed germination % | 90 | 75 |
| Growth habit | Erect | Erect |
| Phyllanthin content | 0.70-0.77 | 0.30-0.36 |
| Hyphophyllanthin content | 0.32-0.37 | 0.12-0.17 |

TABLE 2

Mean performance of selected mutant lines for fresh herb yield in grams

| | Initial evaluation trials | | | Advanced trials | | |
| --- | --- | --- | --- | --- | --- | --- |
| Entries | 2001(0.9 sqm) | 2001(0.9 sqm) | Mean | 2002(1.8 sqm) | 2002(1.8 sqm) | Mean |
| CIM-Jeevan | 1060 | 1090 | 1075 | 2000 | 2070 | 2035 |
| 'CIM/PAG-1' | 770 | 780 | 775 | 1420 | 1490 | 1455 |
| CD at 1% | 88.44 | 102.35 | | 64.22 | 92.49 | |

The strain CIM/PA36 (subsequently named as CIM-Jeevan) consistently showed higher herbage, phyllanthin and hypophyllanthin in IET and AVT. The herb yield of the cultivar CIM-Jeevan was estimated to be 1.0-1.15 kg per sqm compared to the check 'CIM/PAG-1' 0.79-0.83 kg per sqm. All the yields were higher over the control taken for comparison. The cultivar CIM-Jeevan produced higher phyllanthin and hypophyllanthin in the dry herb (0.70-0.77, 0.32-0.37% respectively) compared to the control (0.30-0.36, 0.12-0.17% respectively).

(iv) Uniformity and Stability

When the uniform plant population of CIM-Jeevan is grown 100 m away from other genotypes of *Phyllanthus amarus* the plants self-pollinates among themselves. Instead the population purity is being maintained through self-pollination within themselves. In the present invention the purity of the plant cultivar was maintained by growing the plant population with an isolation distance of 100 m from other genotypes. The stability of the plant population was checked through DNA profiling using 20 MAP primers in subsequent generations and found to be uniform without variation. The sequences of the primers were AAATCGGAGC (SEQ ID NO.: 1), GTCCTACTCG (SEQ ID NO.: 11), GTCCTAGCG (SEQ ID NO.: 12), TGCGCGATCG (SEQ ID NO.: 2), AACGTACGCG (SEQ ID NO.: 3), GCACGCCGGA (SEQ ID NO.: 13), CACCCTGCGC (SEQ ID NO.: 14), CTATCGCCGC (SEQ ID NO.: 15), CGGGATCCGC (SEQ ID NO. :4), GCGAATTCCG (SEQ ID NO.: 5), CCCTGCAGGC (SEQ ID NO.: 6), CCAAGCTTGC (SEQ ID NO.: 7), GTGCAATGAG (SEQ ID NO.: 16), AGGATACGTG (SEQ ID NO.: 17), AAGATAGCGG (SEQ ID NO.: 8), GGATCTGAAC (SEQ ID NO.: 9), TTGTCTCAGG (SEQ ID NO.: 18), CATCCCGAAC (SEQ ID NO.: 19), GGACTCCACG (SEQ ID NO.: 10), AGCCTGACGC (SEQ ID NO.: 20), respectively. The primers AAATCGGAGC (SEQ ID NO.: 1), TGCGCGATCG (SEQ ID NO.: 2), AACGTACGCG (SEQ ID NO.: 3), CGGGATCCGC (SEQ ID NO.: 4), GCGAATTCCG (SEQ ID NO.: 5), CCCTGCAGGC (SEQ ID NO.: 6), CCAAGCTTGC (SEQ ID NO.: 7), AAGATAGCGG (SEQ ID NO.: 8), GGATCTGAAC (SEQ ID NO.: 9), GGACTCCACG (SEQ ID NO.: 10) were used to develop the unique fingerprint pattern of the cultivar and the pattern was found to be consistent for three generations. The 20 MAP primers were used to differentiate the cultivar CIM-Jeevan from other genotypes (CIM/PAG-1, CIM/NPA24, CIM/PA 117). From RAPD analysis the profiles were studied and similarity indices were calculated which were put into a matrix. As represented in the similarity matrix the cultivar of the invention is quite different from the other varieties.

TABLE 3

Similarity indices of the cultivar 'CIM-Jeevan' compared to other checks.

|  | CIM/PAG-1 | CIM/NPA24 | CIM-Jeevan | CIM/PA117 |
|---|---|---|---|---|
| CIM/PAG-1 | 1.00 | | | |
| CIM/NPA24 | 0.434 | 1.000 | | |
| CIM-Jeevan | 0.536 | 0.751 | 1.000 | |
| CIM/PA117 | 0.366 | 0.573 | 0.576 | 1.000 |

(v)TTaxonomic Description of the Plant

| | | |
|---|---|---|
| 1. Genus: | *Phyllanthus* | |
| 2. Species: | *amarus* Schum & Thonn. | |
| 3. Family: | Euphorbiaceae | |
| 4. Common name: | Bhumyamalaki, Jatmala | |
| 5. Plant: | Annual herb | |
| 6. Height | 60 to 65 cm | |
| 7. Growth habit | erect | |
| 8. Stem: | Terete, Smooth, green (138C), younger parts-rough | |
| 9. Leaf: | | |
| Colour | Green (127A) upper surface, Lower surface (136D) | |
| Surface | Smooth | |
| Shape | elliptic oblong to obovate | |
| Margin | Ciliate | |
| (b) Tip | Obtuse | |
| (c) Base | Obtuse | |
| Petiole length | 0.3 to 0.7 mm | |
| Length | 6 to 10 mm | |
| Width | 4 to 5 mm | |
| 10. Flowers | | |
| Perianth: | Lobes 5, subequal, elliptic or oblong, Disc 5 roundish | |
| Stamens: | 3, free, filaments connate in a column, anther sessile | |
| Style: | 3, spreading, stigma bi-fid, divergent | |
| 11. Fruit: | Capsule, Obvate-rounded, Yellow green group (144 D) | |
| 12. Seed: | Triangular, longitudinal ribs, transverse striate on back | |

The colour codes are in accordance with the "RHS colour chart published by The Royal Horticultural Society, 80 Vincent Square, London SW1P 2PE, 1995. FIG. 1 represents a plant of CIM-Jeevan in the field (30 days old) and FIG. 2 represents the unique RAPD profile of the cultivar.

The invention claimed is:

1. A cultivar of *Phyllanthus amarus* 'CIM-Jeevan', producing high amount of herb, phyllanthin and hypophyllanthin, wherein said cultivar is developed through γ-irradiation of superior germplasm, having following characters:
 a. the said plant produces high amount of herbage yield ranging between 1.0-1.15 kg per sqm fresh total plant herb,
 b. the said plant possesses high vegetative erect growth with a height ranging between 60 to 65 cm,
 c. the said plant has distinct molecular profile established by Random Amplified Polymorphic DNA (RAPD),
 d. the said plant has leaves with following characteristics,
  Color: greenish leaves with upper surface (127A) and lower surface (136D),
  Surface: Smooth,
  Shape: elliptic oblong to obvate,
  Margin: ciliate,
  Tip: obtuse,
  Base: Obtuse,
  Petiole length: 0.3-0.7 mm,
  Length: 6 to 10 mm, and
  Width: 4 to 5 mm
 e. the said plant has stem with following characteristics,
  Terete,
  Smooth,
  Green (138C)
  Young parts are rough
 f. the said plant has flowers with perianth having the following characters:
  Lobes 5, sub-equal, elliptic or oblong, Disc 5 roundish
  Stamens: 3, free, filaments connate in a column, anther sessile
  Style: 3, spreading, stigma bi-fid, divergent
 g. the said plant has fruit with the following characters:
  a. Capsule,
  b. Obvate-rounded,
  c. Yellow green group (144 D)
 h. the said plant has seeds with the following characters:
  a. Triangular,
  b. longitudinal ribs,
  c. transverse striate on back,
  d. weight of 1000-seed: about 1.8 g,
 i. the said plant produce phyllanthin ranging between 0.70-0.77% in dry herb,
 j. the said plant produce hypophyllanthin ranging between 0.32-0.37% in dry herb,
 k. the said plant produce average dry seed per plant of about 4.1 in grams,
 l. the said plant produce average dry leaves per plant of about 5.75 in grams,
 m. the said plant produce average dry biomass per plant of about 11 in grams,
 n. the said plant produce average fresh biomass per plant at harvest of about 55 in grams,
 o. the said plant shows seed germination of about 90%, and
 p. the said plant is an annual herb.

\* \* \* \* \*

SEQUENCE LISTING

<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aaatcggagc                                                          10

```
<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgcgcgatcg                                                           10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aacgtacgcg                                                           10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggatccgc                                                           10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgaattccg                                                           10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccctgcaggc                                                           10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaagcttgc                                                           10

<210> SEQ ID NO 8
```

<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagatagcgg                                                              10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggatctgaac                                                              10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggactccacg                                                              10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtcctactcg                                                              10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtccttagcg                                                              10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcacgccgga                                                              10

<210> SEQ ID NO 14
<211> LENGTH: 10

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccctgcgc                                                            10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctatcgccgc                                                            10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtgcaatgag                                                            10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aggatacgtg                                                            10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttgtctcagg                                                            10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catcccgaac                                                            10

<210> SEQ ID NO 20
<211> LENGTH: 10
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 20
agcctgacgc                                                              10
```